United States Patent [19]

Strenk et al.

[11] Patent Number: 5,706,812

[45] Date of Patent: Jan. 13, 1998

[54] STEREOTACTIC MRI BREAST BIOPSY COIL AND METHOD FOR USE

[75] Inventors: Susan A. Strenk; Lawrence M. Strenk, both of Aurora, Ohio; Reuben S. Mezrich, Skillman, N.J.

[73] Assignee: Diagnostic Instruments, Inc., Twinsburg, Ohio

[21] Appl. No.: 562,564

[22] Filed: Nov. 24, 1995

[51] Int. Cl.$^6$ ................................................ A61B 5/055
[52] U.S. Cl. .......................... 128/653.5; 128/653.2; 324/318
[58] Field of Search .................. 128/653.2, 653.5; 324/318, 322

[56] References Cited

U.S. PATENT DOCUMENTS

| | | |
|---|---|---|
| 4,897,604 | 1/1990 | Carlson et al. . |
| 4,958,936 | 9/1990 | Darrasse et al. . |
| 5,050,605 | 9/1991 | Eydelman et al. . |
| 5,085,219 | 2/1992 | Ortendahl et al. . |
| 5,304,933 | 4/1994 | Vavrek et al. . |
| 5,311,868 | 5/1994 | Carbini et al. . |
| 5,437,280 | 8/1995 | Hussman ............................. 128/653.2 |

OTHER PUBLICATIONS

Michael D. Harpen, "Sample noise with circular surface coils", Jul./Aug. 1987, pp. 616–618.

Michael D. Harpen, "Analysis of capacitive coupling and associated loss for a solenoidal magnetic resonance imaging radio-frequency coil", Mar./Apr. 1989, pp. 234–238.

Steven E. Harms, MD, et al., "MR Imaging of the Breast", Jan./Feb. 1993, pp. 277–283.

Sylvia H. Heywang-Kobrunner, et al., "Contract-Enhanced MRI of the Breast after Limited Surgery and Radiation Therapy", Nov./Dec. 1993, pp. 891–900.

Sylvia H. Heywang-Kobrunner, MD, et al., "Prototype Breast Coil for MR-Guided Needle Localization", 1994, pp. 876–881.

Sylvia H. Heywang-Kobrunner, MD, "Contrast-Enhanced Magnetic Resonance Imaging of the Breast", Jan. 1994, pp. 94–104.

Sylvia H. Heywang-Kobrunner, MD, et al., "Contrast-enhanced MR Imaging of the Breast: Comparison of Two Different Doses of Gadopenetate Dimeglumine", Jun. 1994, pp. 639–646.

Uwe Fischer, MD, et al., "MR-guided Biopsy of Suspect Breast Lesions with a Simple Stereotaxic Add-on Device for Surface Coils", Jul. 1994, pp. 272–273.

Susan Greenstein Orel, MD, et al., "MR-Imaging-guided Localization and Biopsy of Breast Lesions: Initial Experience", Oct. 1994, pp. 97–102.

Official Gazette, Oct. 25, 1994, pp. 2396–2397.

Mitchell D. Schnall, MD, PhD, et al., "MR Guided Biopsy of the Breast", Nov. 1994, vol. 2, No. 4, pp. 585–589.

Official Gazette, Jan. 10, 1995, p. 888.

Uwe Fischer, MD, et al., "MR Imaging-guided Breast Intervention: Experience with Two Systems", May 1995, pp. 533–538.

NM deSouza MD, "Frameless Stereotactic Breast Biopsy", Workshop in Breast MR, Jun. 24–25, 1995, Cover Page and p. 30.

Susan Greenstein Orel, MD, et al., "Staging of Suspected Breast Cancer: Effect of MR Imaging and MR-guided Biopsy", Jul. 1995, pp. 115–122.

Stuart G. Silverman, MD, et al., "Interactive MR-guided Biopsy in an Open-Configuration MR Imaging System", Oct. 1995, pp. 175–181.

Reuben Mezrich, MD, PhD, "Interventional MRI rides wave of new technology", Oct. 1995, pp. MR28–MR32.

*Primary Examiner*—Marvin M. Lateef
*Assistant Examiner*—Eleni Mantis Mercader
*Attorney, Agent, or Firm*—Pearne, Gordon, McCoy & Granger LLP

[57] ABSTRACT

An MRI breast coil is provided with a large transverse access portal and a stereotactic frame for guiding a biopsy needle. The portal is covered by thin sheath of plastic to retain the breast but still allow insertion of the needle to any location. The frame aligns the needle by azimuth, height and depth.

15 Claims, 3 Drawing Sheets

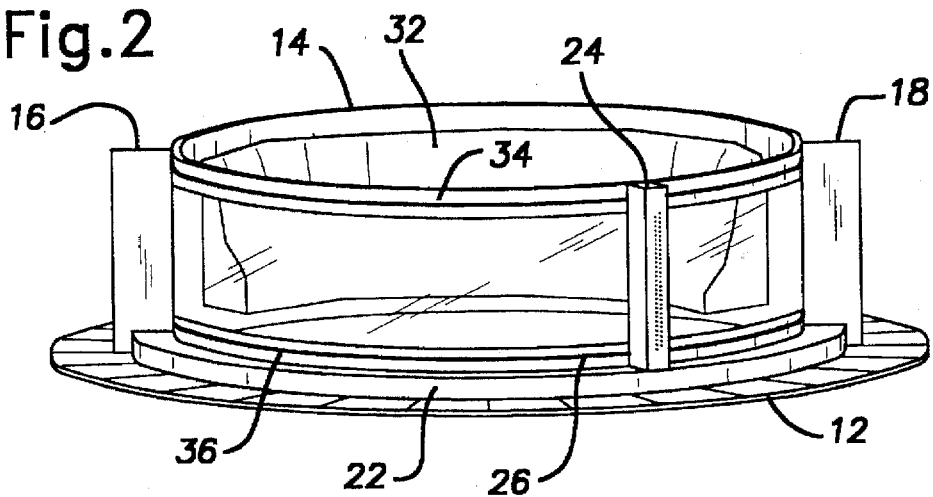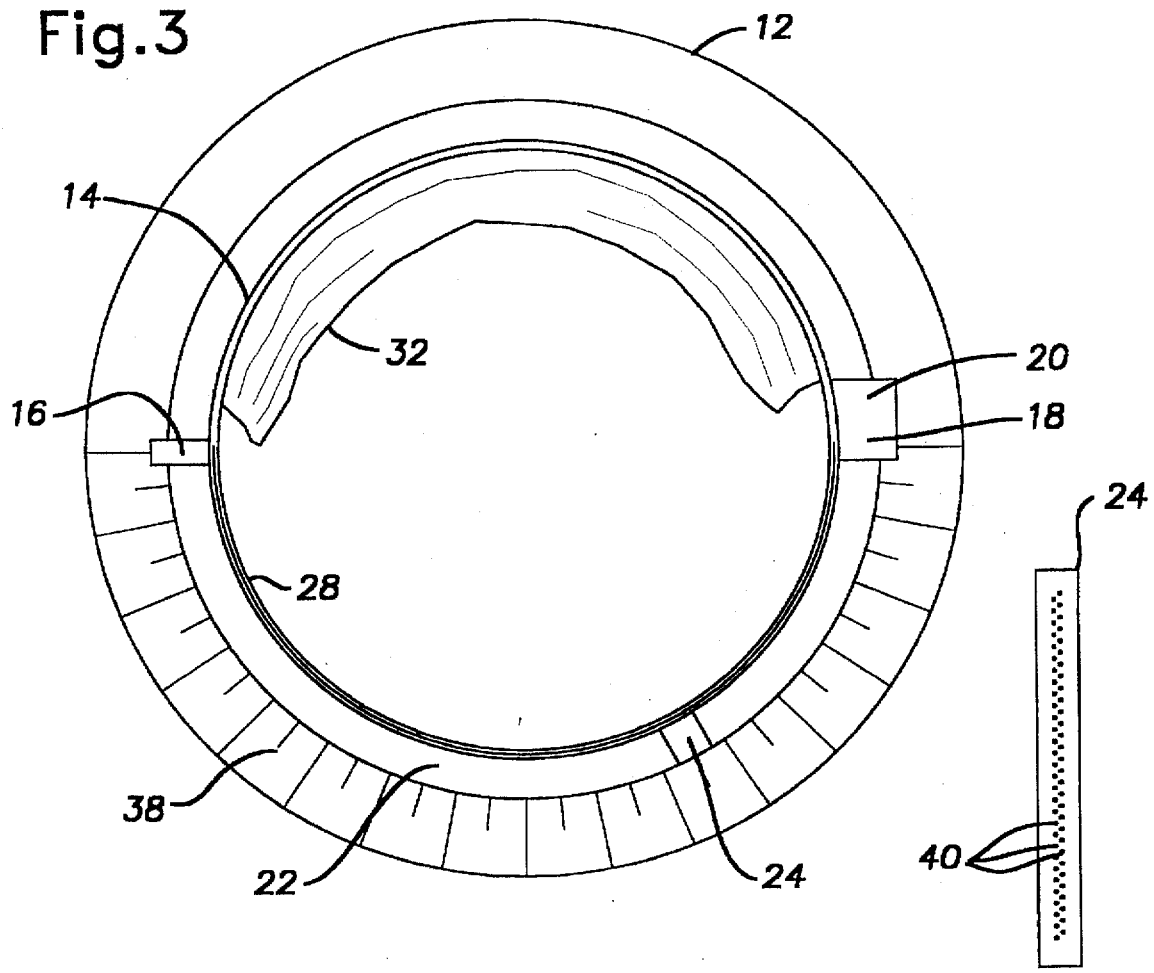

STEREOTACTIC MRI BREAST BIOPSY COIL AND METHOD FOR USE

BACKGROUND OF THE INVENTION

The present invention relates to MRI-guided tissue biopsy and, in particular, to a stereotaxic breast biopsy coil.

Magnetic resonance imaging (MRI) can detect breast malignancies that have previously been sub-clinical (i.e., neither palpable nor detected by mammography). Unfortunately, a 40 percent false positive rate goes along with this detection. This results in a large number of extremely invasive open biopsies being performed.

It is desirable to use less invasive methods such as a needle biopsy (core or aspiration), but needle placement requires 1 mm accuracy in three dimensions.

SUMMARY OF THE INVENTION

An MRI coil for providing an image of a protuberance of tissue has a tubular wall having a longitudinal proximal portion adapted to receive the protuberance and a longitudinal distal portion. The wall includes a transverse access portal between the distal and proximal portions. This portal eliminates a substantial portion of the wall. A first coil portion is located about the distal portion and a second coil portion is located about the proximal portion.

BRIEF DESCRIPTION OF THE DRAWINGS

FIG. 2 is a front perspective view of a coil according to the invention.

FIG. 3 is a top plan view of the a coil according to the invention.

FIG. 4 is front elevation view of a needle guide according to the invention.

DESCRIPTION OF THE PREFERRED EMBODIMENTS

Figure 1:
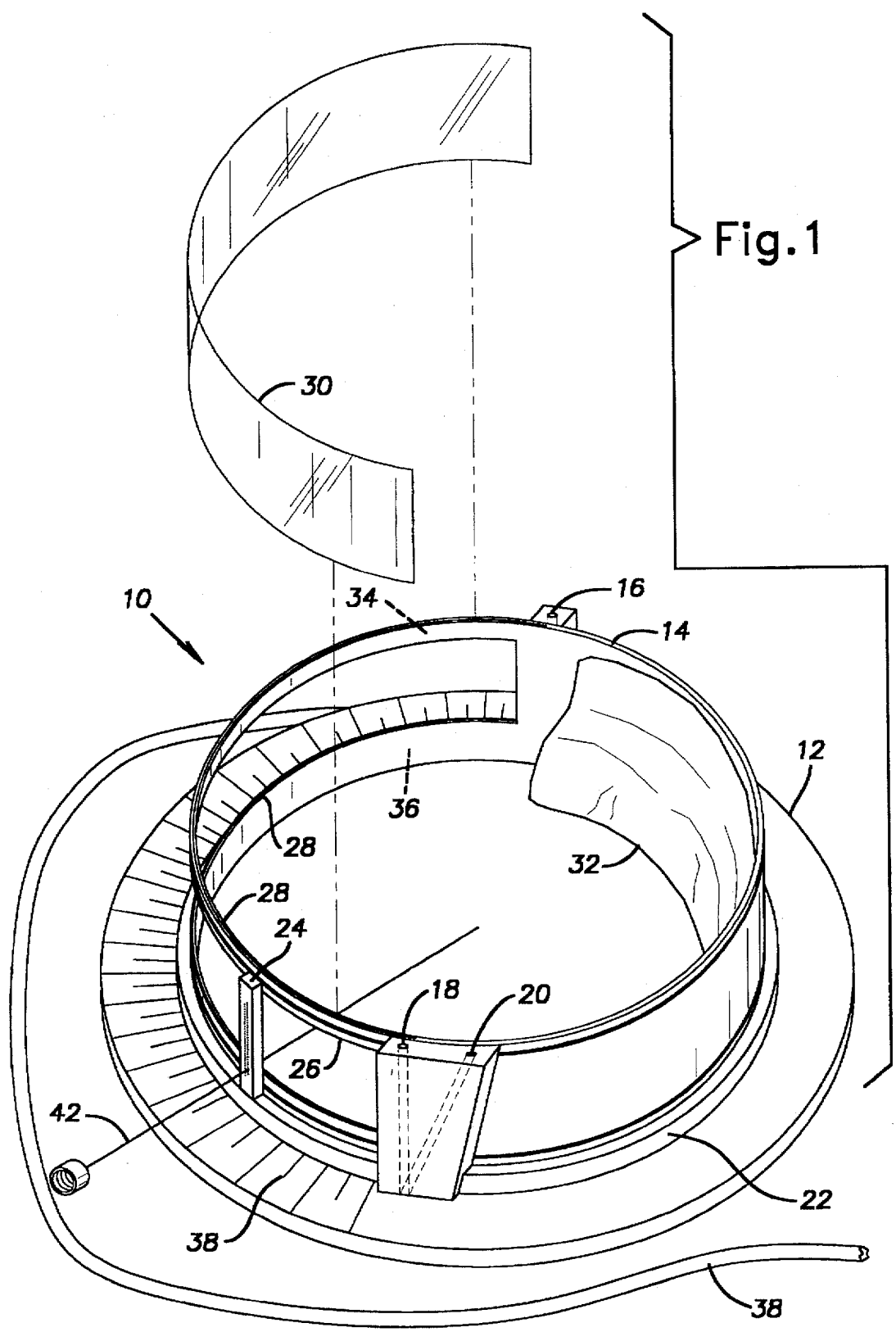
FIG. 1 is a perspective view of a coil according to the invention from above with a portion exploded.

Referring to FIGS. 1, 2 and 3, a breast biopsy coil 10 includes a base 12 to which is attached a tubular wall 14 and three fiducials 16, 18, 20.

A ring 22 abuts the external junction of the base 12 and the wall 14. The ring 22 is rotatable about its axis and is slidably retained between the fiducials 16, 18, 20 and base 12 and wall 14. A needle guide 24 is removably attached to the ring 22. These structures can be formed from a suitable non-magnetic, MRI transparent material such as a thermoplastic polymer of methyl methacrylate (e.g., Plexiglas).

The wall 14 includes a large aperture or portal 26. The wall 14 contains a slot 28 for receiving a sheath 30. The sheath 30 may be, for example, a thin sheet of plastic of moderate stiffness and being relatively easy to puncture with a sharp instrument (e.g., 15 mil thick polyurethane film such as TEXIN brand polyurethane film from Bayer Polymers Division, Bayer Corporation, or ⅟₃₂ inch thick Huntsman High Impact Polystyrene—Medical Grade).

The interior of the wall opposite the portal 26 is provided with an inflatable bladder 32. The bladder 32 may be, for example, formed of latex rubber.

The coil 10 may have, for example, an internal diameter of 17.8 cm and a height of 7 cm. This provides an internal volume of about 1740 ml for ease of breast placement. When the bladder 32 is fully inflated, this volume may be, for example, reduced to 900 ml.

The proximal portion of the wall 14 contains a portion 34 of an electrical coil about its circumference. Similarly, the distal portion of the wall 14 contains a portion 36 of an electrical coil about its circumference. The electrical coil portions 34, 36 may be, for example, single turns. The electrical coil portions are connected by an unshown matching network to a cable 38 and include capacitive splits, a detuning diode, and current traps to protect the coil during transmission by an unshown imager. Such features are set forth in U.S. patent application Ser. No. 08/530,576, filed Sep. 19, 1995, and incorporated herein by reference. The coil may operate, for example, at 63.89 MHz. The distal and proximal coil portions allow for the portal to be, for example, 5.7 cm high and to extend around nearly 180 degrees of the wall 14.

The base 12 can be provided with a graduated scale 38 to provide an azimuthal positioning of the needle guide 24 as the ring 22 is rotated.

Referring to FIG. 4, the needle guide 24 has a series of guide bores 40. The bores 40 are in two staggered rows to provide increased spatial resolution. For use with an 18 gauge needle (nominally 1 mm), the bores 40 are bored 0.07 mm over needle size. They are on 2 mm centers with the staggering providing plus or minus 0.5 mm resolution in the vertical direction. A different guide 24 is provided for each size needle to be used. The guide 24 can be conveniently made, to insert into a receptacle in the ring 22. The number of staggered rows can be varied to insure the desired resolution for different needle/bore sizes.

In general, a needle 42 inserted into the guide 24 will follow a radial path with respect to the ring 22. The graduations scale 38 may be, for example, spaced to provide 1.5 mm arc length at the interior of the wall 14. This then provides a resolution of plus or minus 0.77 mm at the wall 14 and as the needle tip continues to the center the resolution approaches zero.

The depth of insertion of the needle 42 can be conveniently determined, for example, by either a graduated scale on the needle or a moveable stop placed on the needle to prevent further insertion through a guide bore 40.

The combination of adjusting the ring 22 in azimuth, choosing the proper guide bore 40 and inserting the needle 42 a desired depth into the guide bore can easily provide better than 1 mm resolution for positioning the needle tip in three dimensions within the coil 10.

The vertical fiducials 16, 18 consist of 5 mm bores parallel to the axis the coil 10. The fiducials 16, 18 are located on a diameter of the ring 22. The fiducial 20 consists of a 5 mm bore at an angle to the fiducial 18. The bores of the fiducials 18, 20 intersect to form the zero height reference of the coil 10. The angle between the fiducials 18, 20 may be, for example, 45 degrees. The bores are filled with a material that will provide an MRI image, for example, 0.04M $CuSo_4 \cdot 5H_2O$.

In operation, a breast or other protuberance of tissue is inserted into the proximal portion 34 of the wall 14 and extends toward the distal portion 36. In the preferred embodiment, the patient lies in a prone position upon the coil 10 (with suitable surrounding support).

The bladder 32 is inflated by unshown means to compress the breast against the portal 26. The sheath 30 keeps the breast from "leaking" in a transverse direction out of the portal 26. The sheath 30 provides support of the lateral portion of breast. Despite the large portal 24, there is no compromise of immobilization. The sheath 30 is readily replaceable between patients or procedures.

Figure 5:
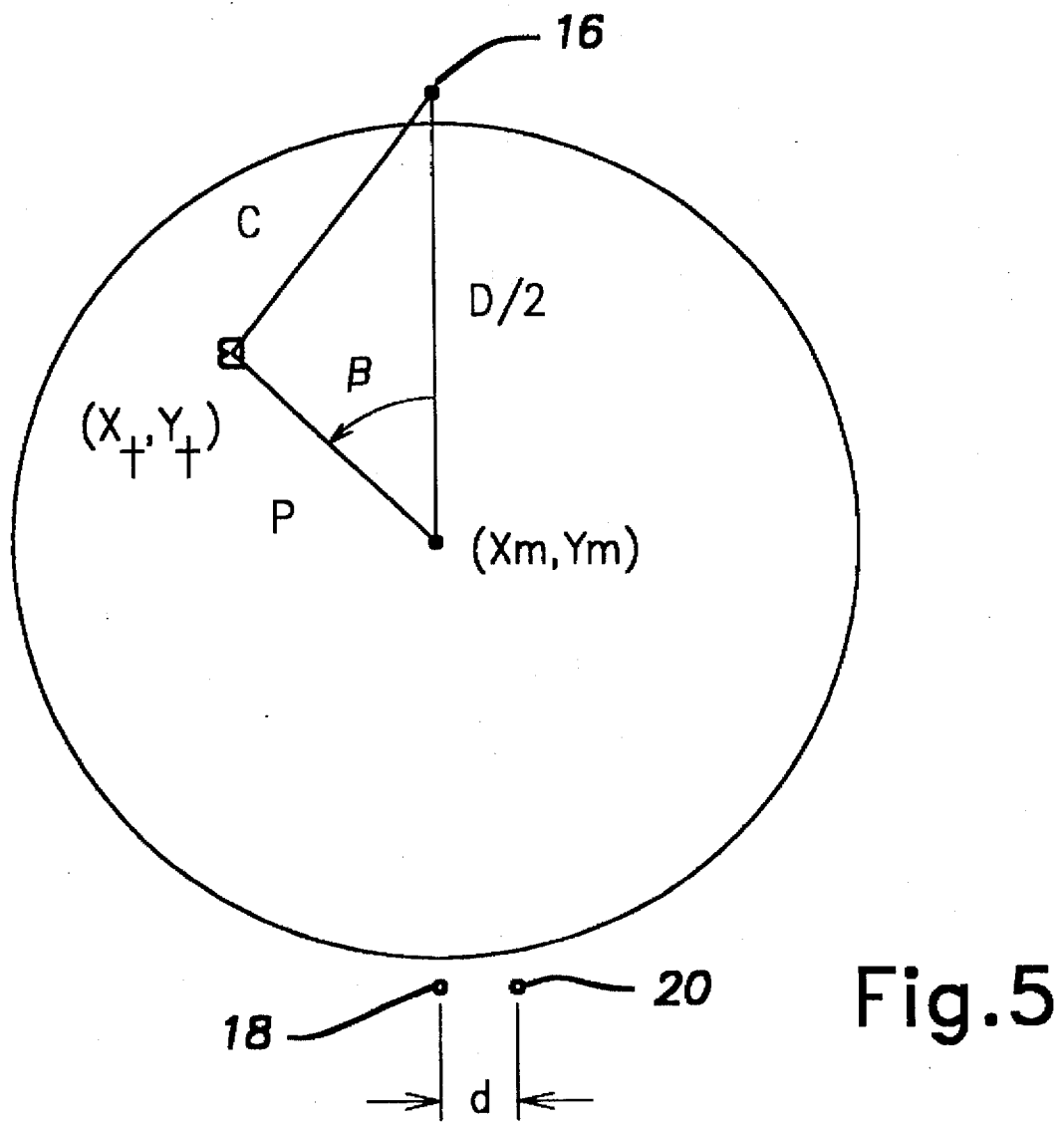
FIG. 5 is a graphical view of the geometry of an embodiment of the invention.

The breast is then imaged using the coil 10 with an unshown MRI imager. Referring to FIG. 5, in a coronal image, the fiducials 18, 20 produce dots separated by a distance d. The height h above the base of the coil is given by: $h=d \cdot \tan(45°)$.

If the coordinates of the fiducials 16, 18 are $(x_1, y_1)$ and $(x_2, y_2)$, respectively, then the midpoint between them $(x_m, y_m)$ is given by: $(x_m, y_m)=((x_1+x_2)/2, (y_1+y_2)/2)$. The distance between the fiducials 16, 18 is D given by: $D=((x_1-x_2)^2+(y_1-y_2)^2)^{1/2}$.

The distance $\rho$ from the midpoint to the imaged lesion or target $(x_t, y_t)$ is given by: $\rho=((x_t-x_m)^2+(y_t-y_m)^2)^{1/2}$. The distance c from the fiducial 16 to the target is given by $c=((x_t+x_2)^2+(y_t+y_2)^2)^{(1/2)}$. The azimuthal angle $\beta$ is given by: $\beta=\arccos((c^2-\beta^2-(D/2)^2)/(-2 \cdot \beta \cdot (D/2)))$.

The needle insertion length N is given by: $N=R-\rho$ where R is the length of the needle. Thus the image can be used to provide the anteroposterior distance, the needle insertion length, and the angular position necessary to locate the target in three dimensions and insert the tip the needle 42 to that location.

Based on the data from the image, the needle guide 24 is rotated to the correct azimuth and the needle inserted into the correct guide bore 40. The needle 42 is then inserted through the sheath 30 into the breast (the needle and sheath are sterile) to the desired depth. For particularly large bore needles, the breast skin (and the sheath) can be nicked to assist in inserting the needle. The tip of the needle is then located within less than 1 mm of the desired location.

A biopsy of the lesion can be performed by using either a coring biopsy needle or an aspiration biopsy needle. In addition, because of MRI detects tumor borders more accurately than other modalities, the needle can be used to localize the lesion.

The large portal 24 provides ready access to any point within the breast and makes such procedures as skin nicks easy to accomplish. This large portal 24 is made possible by the sheath 30.

The sheath 30 provides support and immobilization for the tissue, while still permitting access to any location of the tissue with needles or other puncturing or cutting instruments. This combination of portal and sheath can be used in other coil/frame structures, for example, a tubular wall having an oval or rectangular cross-section, or a frustoconical chamber can be conveniently provided with a large portal that can be covered with a sheath.

In the preferred embodiment, the necessary position settings for the needle 42 are automatically calculated by either software in the imager or in an auxiliary computer such as a laptop computer.

The coil 10 as described provides needle access to within about 1 cm of the chest wall. If access to the blocked area is desired, the needle guide 24 can be provided with guide bores at a polar angle to the plane of the coil. With minor modifications to the calculations, the needle can then be accurately inserted into this area.

Other configurations of the invention are also possible, for example, the electrical coil portions 34, 36 can be provided in the form of a separate electrical coil or coils that are placed about the coil 10 during operation. The coil 10 is then more accurately described as a frame even though its structure remains otherwise unchanged. This structure provides a stereotactic frame for orienting a needle. It also may be advantageous to use the coil 10 in combination with additional electrical coil geometries (e.g., Helmoltz, saddle, or surface coil), either integral or external.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. An MRI coil for providing an image of a protuberance of tissue, said coil comprising:
   a tubular wall having a longitudinal proximal portion adapted to receive said protuberance and a longitudinal distal portion, said wall including a transverse access portal between said distal and proximal portions, said portal eliminating a substantial portion of said wall;
   a puncturable sheath closing said portal, said sheath being readily replaceable;
   a first coil portion about said distal portion; and
   a second coil portion about said proximal portion.

2. A coil according to claim 1, further comprising a fiducial reference providing a correspondence between said image and the interior of said tubular wall.

3. A coil according to claim 1, further comprising a bladder inside said wall, said bladder being inflatable to urge said protuberance toward said portal.

4. A coil according to claim 1, further comprising a member constrained to move azimuthally about an axis extending longitudinally within said wall; and a needle guide connected to said member, said guide including a plurality of guide bores for locating a needle in a plurality of longitudinal positions between said proximal and distal portions.

5. (amended) A stereotactic frame for orienting a needle, said frame comprising:
   a base;
   a member constrained to move azimuthally about an axis extending transversely from said base;
   a needle guide connected to said member for locating said needle in a plurality of positions spaced away from said base;
   a tubular wall having a longitudinal proximal portion adapted to receive said protuberance and a longitudinal distal portion, said wall being attached to said base and including a transverse access portal between said distal and proximal portions; and
   a puncturable sheath closing said portal, said sheath being readily replaceable.

6. A frame according to claim 5, further comprising a fiducial reference providing a correspondence between an MRI image and said frame.

7. A frame according to claim 5, further comprising a plurality of needle guides, each needle guide having a different size of guide bores and being interchangeably connectable to said member.

8. A frame according to claim 5, further comprising a bladder inside said wall, said bladder being inflatable to urge said protuberance toward said portal.

9. A frame for immobilizing a protuberance of tissue, said frame comprising:
   at least one wall having a longitudinal proximal portion closest to said protuberance and a longitudinal distal portion, said wall including a transverse access portal between said distal and proximal portions, said portal eliminating a substantial portion of said wall; and a puncturable sheath closing said portal, said sheath being readily replaceable.

10. A frame for immobilizing a protuberance of tissue, said frame comprising:

a wall having a longitudinal proximal portion adapted to receive and engirdle said protuberance and a longitudinal distal portion, said wall including a transverse access portal between said distal and proximal portions, said portal eliminating a substantial portion of said wall; and a puncturable sheath closing said portal, said sheath being readily replaceable.

11. A frame according to claim 10, further comprising a bladder inside said wall, said bladder being inflatable to urge said protuberance toward said portal.

12. A frame according to claim 10, further comprising a fiducial reference providing a correspondence between an MRI image and the interior of said wall.

13. An MRI coil for providing an image of a protuberance of tissue, said coil comprising:

a tubular wall having a longitudinal proximal portion adapted to receive said protuberance and a longitudinal distal portion, said wall including a transverse access portal between said distal and proximal portions, said portal eliminating a substantial portion of said wall;

a first coil portion about said distal portion;

a second coil portion about said proximal portion;

a fiducial reference providing a correspondence between said image and the interior of said tubular wall;

a puncturable sheath closing said portal, said sheath being readily replaceable;

a bladder inside said wall, said bladder being inflatable to urge said protuberance toward said portal;

a member constrained to move azimuthally about an axis extending longitudinally within said wall; and a needle guide connected to said member, said guide including a plurality of guide bores for locating a needle in a plurality of longitudinal positions between said proximal and distal portions.

14. A method for maneuvering a needle to a location indicated in an MRI image of a protuberance of tissue, said method comprising:

providing an MRI coil for providing said image;

providing a stereotactic frame, said frame including:

a tubular wall having a longitudinal proximal portion adapted to receive said protuberance and a longitudinal distal portion, said wall including a transverse access portal between said distal and proximal portions, said portal eliminating a substantial portion of said wall;

a fiducial reference providing a correspondence between said image and the interior of said tubular wall;

a puncturable sheath closing said portal, said sheath being readily replaceable;

a member constrained to move azimuthally about an axis extending longitudinally within said wall; and a needle guide connected to said member, said guide including a plurality of guide bores for locating a needle in a plurality of longitudinal positions between said proximal and distal portions;

inserting said protuberance into said proximal portion;

imaging said protuberance and said fiducial reference;

determining the correspondence between said location and the interior of said tubular wall;

moving said needle guide to an azimuth intersecting said location;

placing said needle into a guide bore intersecting said location; and inserting said needle through said sheath to a depth intersecting said location.

15. A method according to claim 14, further comprising:

further including in said frame a bladder inside said wall and;

inflating said bladder to urge said protuberance toward said portal.

* * * * *

UNITED STATES PATENT AND TRADEMARK OFFICE
CERTIFICATE OF CORRECTION

PATENT NO. : 5,706,812
DATED : January 13, 1998
INVENTOR(S) : Susan A. Strenk, et al.

It is certified that error appears in the above-identified patent and that said Letters Patent is hereby corrected as shown below:

Column 2, line 30, after "made", please delete --,--.

Column 3, line 13, please delete "$(y_{1-y2})$" and insert therefor --$(Y_1-Y_2)$--.

Column 3, line 17, after "$(y_t+y_2)^2$", please delete --$)^2$--.

Column 3, line 18, after "$c^2-$", please delete "$\beta^2$" and insert therefore --$\rho^2$--.

Column 3, line 18, after "/-2·", please delete "$\beta$" and insert therefor --$\rho$--.

Column 4, line 38, please delete "(amended)".

Signed and Sealed this

Fourth Day of August, 1998

BRUCE LEHMAN

Attest:

Attesting Officer

Commissioner of Patents and Trademarks